(12) United States Patent
Breitenbach et al.

(10) Patent No.: US 8,841,303 B2
(45) Date of Patent: Sep. 23, 2014

(54) MELT-PROCESSED IMATINIB DOSAGE FORM

(75) Inventors: Jörg Breitenbach, Mannheim (DE); Norbert Steiger, Lingenfeld (DE); Harald Hach, Oberotterbach (DE); Ulrich Westedt, Schriesheim (DE); Martin Knobloch, Neuhofen (DE); Ralf Altenburger, Eimeldingen (DE); Nicoletta Loggia, Basel (CH); Jörg Ogorka, Steinen (DE)

(73) Assignees: Abbvie Deutschland GmbH & Co. KG, Wiesbaden (DE); Novartis AG, Basel (CH)

( * ) Notice: Subject to any disclaimer, the term of this patent is extended or adjusted under 35 U.S.C. 154(b) by 653 days.

(21) Appl. No.: 12/447,508

(22) PCT Filed: Nov. 8, 2007

(86) PCT No.: PCT/EP2007/062100
§ 371 (c)(1),
(2), (4) Date: Jun. 2, 2010

(87) PCT Pub. No.: WO2008/055965
PCT Pub. Date: May 15, 2008

(65) Prior Publication Data
US 2010/0240672 A1    Sep. 23, 2010

(30) Foreign Application Priority Data
Nov. 9, 2006  (EP) .................................. 06023367

(51) Int. Cl.
*A61K 31/497* (2006.01)
*A61K 9/20* (2006.01)
(52) U.S. Cl.
CPC ............ *A61K 9/2095* (2013.01); *A61K 9/2054* (2013.01)
USPC .................................................. 514/252.18
(58) Field of Classification Search
USPC .................................................. 514/252.18
See application file for complete search history.

(56) References Cited

U.S. PATENT DOCUMENTS

| 5,601,845 A * | 2/1997 | Buxton et al. ................ 424/495 |
| 2003/0086948 A1 * | 5/2003 | Benameur et al. ............ 424/400 |
| 2006/0275372 A1 * | 12/2006 | Jenkins et al. ................ 424/489 |

FOREIGN PATENT DOCUMENTS

| WO | WO-99/03854 | 1/1999 | | |
| WO | WO-03/090720 | 11/2003 | | |
| WO | WO-2006/040779 | 4/2006 | | |
| WO | WO-2006/054314 | 5/2006 | | |
| WO | WO-2006/121941 | 11/2006 | | |
| WO | WO 2006121941 A2 * | 11/2006 | ........... A61K 31/506 |
| WO | PCT/EP2007/062100 | 5/2008 | | |
| WO | WO 2006/121941 | * 11/2011 | ............... A61K 9/20 |

OTHER PUBLICATIONS

Ping, B. et al. Journal of Clinical Oncology vol. 22 pp. 935-942. Published 2004.*
New Drug Application: Imatinib. Published Apr. 12, 2001.*
Schick M.J. in Nonionic Surfactants, pp. 443-445, Marcel Dekker, NY (1987).*
H. Monet, et al. "Formulation Technology. Emulsions, Suspensions, Solid Forms" Wiley VCH, XP002445079 pp. 70-73 and 103 (2001).
D. Leveque, et al., "Clinical Pharmacokinetics of Imatinib Mesylate" *in vivo* 19:77-84 (2005).
H. Mollet, et al. "Formulation Technology. Emulsions, Suspensions, Solid Forms" Wiley VCH, XP002445079 pp. 70-73 and 103 (2001).
ISR (PCT/ISA/210) issued in PCT/EP2007/062100, May 15, 2008, Abbott GmbH & Co. KG

* cited by examiner

*Primary Examiner* — Paul Zarek
*Assistant Examiner* — George W Kosturko
(74) *Attorney, Agent, or Firm* — Saul Ewing, LLP; Peter C. Lauro, Esq.

(57) ABSTRACT

The invention provides a dosage form, comprising a melt-processed mixture of (a) a pharmaceutically effective amount of imatinib or a salt thereof, (b) at least one polymeric binder, and (c) at least one pharmaceutically acceptable non-ionic surfactant. The invention provides imatinib dosage forms with high drug loading which can be prepared in a simple and efficient manner, imatinib dosage forms from which the active principle is released in an essentially pH-independent fashion, and extended release imatinib dosage forms.

17 Claims, 3 Drawing Sheets

*Fig. 1* Example 1
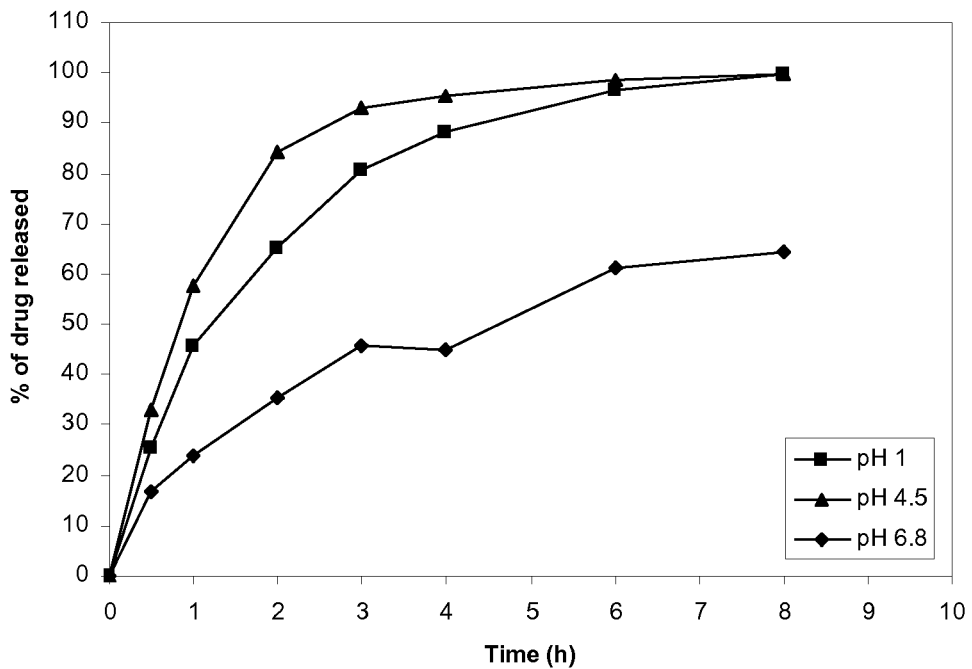
*Fig. 2* Example 2
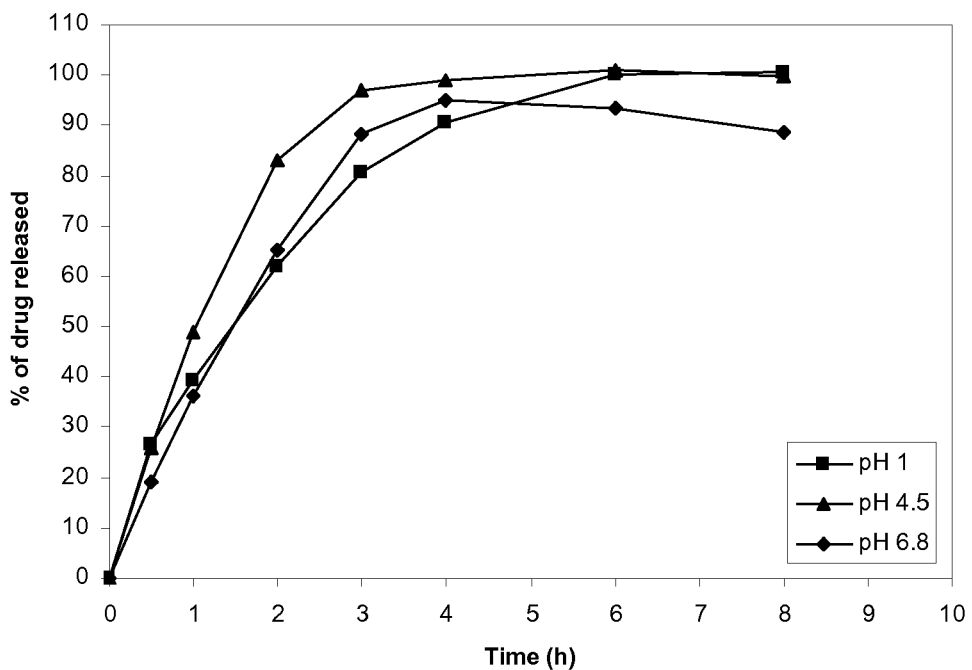

*Fig. 3*   Example 3
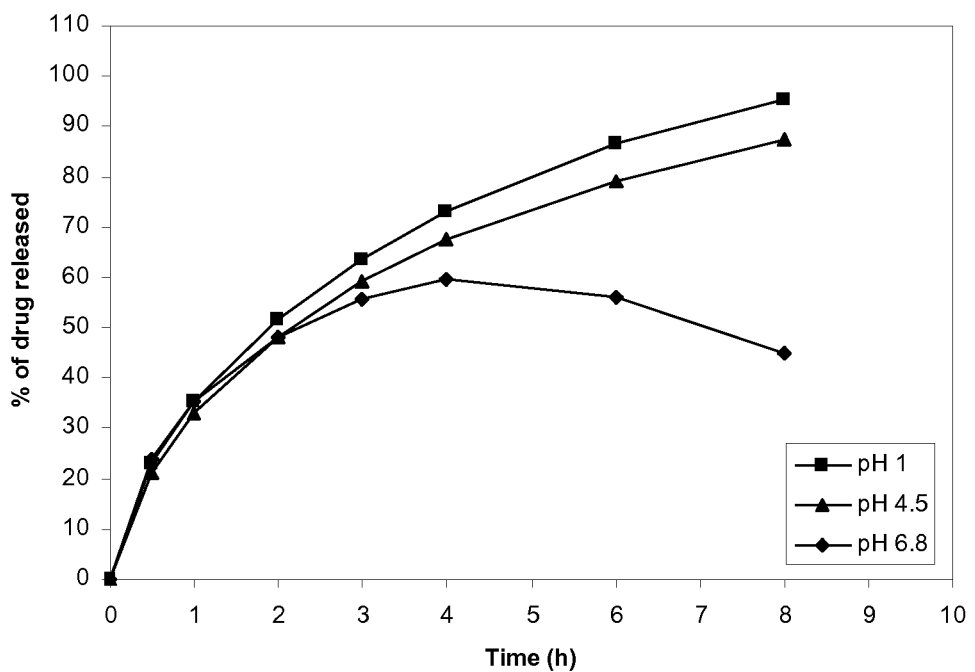
*Fig. 4*   Example 4
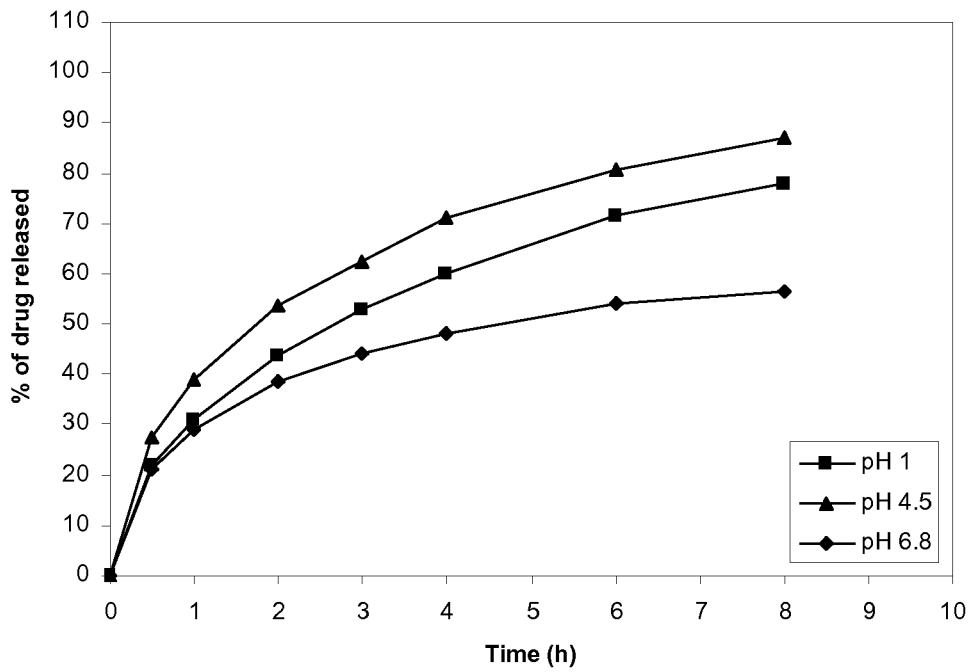

*Fig. 5*   Example 5
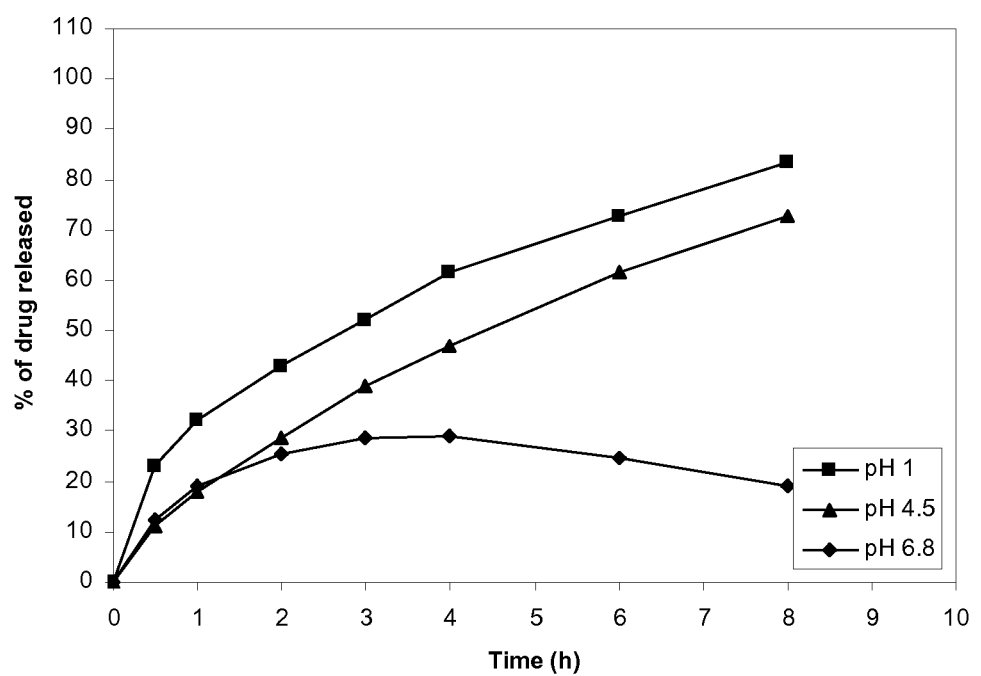

MELT-PROCESSED IMATINIB DOSAGE FORM

This application is the U.S. national phase, pursuant to 35 U.S.C. §371, of PCT international application Ser. No. PCT/EP2007/062100, filed Nov. 8, 2007, designating the United States and published in English on May 15, 2008 as publication WO 2008/055965 A1, which claims priority to European application Ser. No. 06023367.3, filed Nov. 9, 2006. The entire contents of the aforementioned patent applications are incorporated herein by this reference.

The present invention relates to pharmaceutical dosage forms comprising imatinib or pharmaceutically acceptable salts thereof.

Imatinib is a protein tyrosine kinase (PTK) inhibitor used for the treatment of non-malignant and malignant proliferative disorders such as chronic myelogous leukaemia (CML) and gastrointestinal stromal tumors (GIST). The chemical name of imatinib is 4-(4-methylpiperazin-1-ylmethyl)-N-[4-methyl-3-(4-pyridin-3-yl)pyrimidin-2-ylamino)phenyl]-benzamide and it has the formula (I)

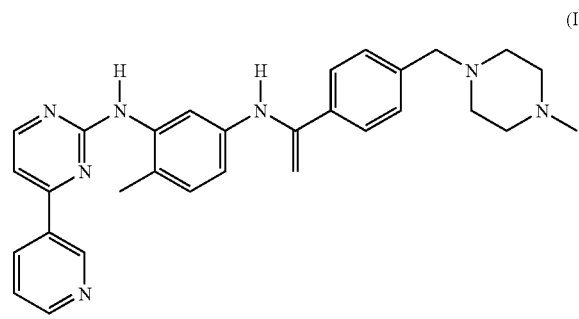 [SMILES: C=C(Nc1ccc(C)c(Nc2nccc(-c3cccnc3)n2)c1)c1ccc(CN2CCN(C)CC2)cc1]

(I)

Imatinib free base and its acceptable salts thereof are disclosed in the European Patent application 0564409. Imatinib mesylate and Imatinib mesylate alpha and beta crystal forms are disclosed in international patent application WO 99/03854.

WO 03/090720 discloses a tablet comprising from 30 to 80% by weight of imatinib based on the total weight of the tablet. The tablet is prepared by a multi-step process which comprises the steps of mixing imatinib or pharmaceutically acceptable salts thereof and pharmaceutically acceptable excipients; wet-granulating; mixing the granulate with excipients; and compressing the mixture to form a tablet.

Due to the presence of several basic nitrogen atoms in its molecular structure, imatinib readily becomes protonated in the presence of acids. Whereas imatinib salts are readily soluble in aqueous media, imatinib free base is less soluble. Therefore, imatinib release from conventional dosage forms is rapid in acid environments and markedly slower in basic environments. This behaviour may be disadvantageous in sustained release dosage forms in which release of the active compound is delayed until when the dosage form reaches the intestine where the increasing pH hampers the dissolution of imatinib.

There is a need for an imatinib dosage form with high drug loading which can be prepared in a simple and efficient manner.

Further, there is a need for an imatinib dosage form from which the active principle is released in an essentially pH-independent fashion.

Further, there is a need for an extended release dosage form comprising imatinib, for example, to reduce peak plasma concentration and to maintain therapeutic plasma levels for a prolonged period of time.

Accordingly, the present invention provides a dosage form, comprising a melt-processed mixture of
(a) a pharmaceutically effective amount of imatinib or a salt thereof, and
(b) at least one polymeric binder, and
(c) at least one pharmaceutically acceptable non-ionic surfactant.

Imatinib may be in the free base form or pharmaceutically acceptable salts thereof.

Pharmaceutically acceptable salts of imatinib include, but are not limited to, addition salts of pharmaceutically acceptable acids. Examples of pharmaceutically acceptable acids include inorganic acids, such as hydrochloric acid, sulphuric acid or phosphoric acid, or organic carboxylic or sulfonic acids, for example aliphatic mono- or dicarboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxy-benzoic acid, salicylic acid, 4-aminsalicylic acid, aromatic-aliphatic carboxylic acids, such as mandelic acid or cinnamic acid, heteroaromatic acids, such as nicotinic acid or isonicotinic acid, aliphatic sulfonic acids, such as methane-, ethane- or 2-hydroxyethane-sulfonic acid, or aromatic sulfonic acids, for example benzene-, p-toluene- or naphthalene-2-sulfonic acid.

In preferred embodiments, an imatinib salt is used, preferably the monomesylate salt of imatinib.

In general, the salt of imatinib is present in the dosage form in predominantly crystalline form. For example imatinib mesylate is present in alpha or beta crystal form, most preferably, in the beta crystal form.

The dosage form according to the invention preferably has a high drug loading to provide a daily dosage amount of imatinib in a form that is convenient to administer. In particular, imatinib or a salt thereof is present in an amount of at least 50% by weight, more preferably at least 55% by weight, e.g. at least 60% by weight based on the total weight of the melt-processed mixture. Typically, the amount of imatinib or a salt thereof may vary up to 80% by weight based on the total weight of the melt-processed mixture. Given the relatively small amount of excipients this enables the production of physically small dosage forms. The dosage forms of the invention are, despite the high drug loading, small, and, therefore, convenient to administer. This leads to a better patient compliance.

According to the present invention, the amount of polymeric binder may vary within a range of from about 1 to 45%, preferably 1 to 38%, in particular 1 to 33% in weight based on the total weight of the melt-processed mixture.

The amount of non-ionic surfactant may vary within a range of from to 5 to 20%, e. g. 7 to 10% in weight based on the total weight of the melt-processed mixture.

The amount of optional ingredients may vary within a range up to 20%, e. g. 1 to 10% in weight based on the total weight of the melt-processed mixture.

The dosage forms according to the invention preferably are sustained release dosage forms. "Sustained release" refers to gradual but continuous or sustained release over a relatively extended period of the active compound content after oral ingestion.

In preferred embodiments, the drug release from the dosage form is not greater than 80% at 1 hour, and not less than 80% at 10 hours, when tested using USP I basket apparatus at 100 rpm in 900 mL of 0.1 hydrochloric acid at 37° C.

In more preferred embodiments, the drug release from the dosage form is not greater than 80% at 2 hour, and not less than 80% at 8 hours, when tested using USP I basket apparatus at 50 rpm in 900 mL of 0.1 hydrochloric acid at 37° C.

In preferred embodiments of the dosage according to the invention, the drug release from the dosage form is essentially independent of pH.

For example, the drug release from the dosage form at 8 hours results in a ratio of a release value at pH 6.8 relative to a release value at pH 1.0 of at least 0.6, when tested using USP I basket apparatus at 50 rpm in 900 mL at 37° C. Suitable buffers having are described in the examples that follow.

In preferred embodiments, the drug release from the dosage form at 8 hours results in a ratio of a release value at pH 6.8 relative to a release value at pH 1.0 of at least 0.7, preferably of at least 0.75, in particular of at least 0.8.

Generally, the polymeric binder employed in the invention has a glass transition temperature Tg of at least about +10° C., preferably at least about +25° C., most preferably from about 40° to 180° C. Methods for determining the Tg values of organic polymers are described in "Introduction to Physical Polymer Science", 2nd Edition by L. H. Sperling, published by John Wiley & Sons, Inc., 1992. The Tg value can be calculated as the weighted sum of the Tg values for homopolymers derived from each of the individual monomers i that make up the polymer, i.e. $Tg=\Sigma W_i X_i$ where W is the weight percent of monomer i in the organic polymer and X is the Tg value for the homopolymer derived from monomer i. Tg values for the homopolymers are indicated in "Polymer Handbook", 2nd Edition by J. Brandrup and E. H. Immergut, Editors, published by John Wiley & Sons, Inc., 1975.

Suitable pharmaceutically acceptable polymers are the following:

homopolymers and copolymers of N-vinyllactams, in particular homopolymers and copolymers of N-vinylpyrrolidone, e.g. polyvinylpyrrolidone (PVP), copolymers of N-vinylpyrrolidone and vinyl acetate or vinyl propionate, cellulose esters and cellulose ethers, in particular methylcellulose and ethylcellulose, hydroxyalkylcelluloses, in particular hydroxypropylcellulose, hydroxyalkylalkylcelluloses, in particular hydroxypropylmethylcellulose, cellulose phthalates or succinates, in particular cellulose acetate phthalate and hydroxypropylmethylcellulose phthalate, hydroxypropylmethylcellulose succinate, hydroxypropylmethylcellulose acetate succinate or hydroxypropylmethylcellulose acetate phthalate;

high molecular weight polyalkylene oxides such as polyethylene oxide and polypropylene oxide and copolymers of ethylene oxide and propylene oxide, polyacrylates and polymethacrylates such as methacrylic acid/ethyl acrylate copolymers, methacrylic acid/methyl methacrylate copolymers, butyl methacrylate/2-dimethylaminoethyl methacrylate copolymers, poly(hydroxyalkyl acrylates), poly(hydroxyalkyl methacrylates), polyacrylamides, vinyl acetate polymers such as copolymers of vinyl acetate and crotonic acid, partially hydrolyzed polyvinyl acetate (also referred to as partially hydrolyzed polyvinyl alcohol), polyvinyl alcohol, oligo- and polysaccharides such as carrageenans, galactomannans and xanthans, or mixtures of one or more thereof.

Of these, homo- or copolymers of vinylpyrrolidone are particularly preferred, e.g. polyvinylpyrrolidone with Fikentscher K values of from 12 to 100, preferably 17 to 30, or copolymers of from 30 to 70% by weight N-vinylpyrrolidone (VP) and 70 to 30% by weight vinyl acetate (VA), such as, for example, a copolymer of 60% by weight VP and 40% by weight VA.

It is, of course, possible to employ mixtures of said polymers.

Preferred polymeric binders are selected from the group consisting of cellulose derivatives, in particular hydroxypropyl cellulose and ethylcellulose, and homo- or copolymers of vinylpyrrolidone, and mixtures thereof.

It is believed that the polymeric binder, apart from imparting physical integrity and sufficient mechanical strength to the dosage forms, acts as a release retardant.

The term "pharmaceutically acceptable surfactant" as used herein refers to a pharmaceutically acceptable non-ionic surfactant. The surfactant may effectuate an instantaneous emulsification of the active ingredient released from the dosage form and/or prevent precipitation of the active ingredient in the aqueous fluids of the gastrointestinal tract.

Preferred surfactants are selected from polyol fatty acid esters such as, for example alkylene glycol fatty acid mono- or diesters, or sorbitan fatty acid esters; polyalkoxylated polyol fatty acid esters such as, for example, polyalkoxylated glycerides, polyalkoxylated sorbitan fatty acid esters or fatty acid esters of polyalkylene glycols, or polyalkoxylated ethers of fatty alcohols.

A fatty acid chain in these compounds ordinarily comprises from 8 to 22 carbon atoms. The polyol may be a diol such as ethyleneglycol or propylenglycol, a triol such as glycerol, or a higher polyol such as sorbitan. The polyalkylene oxide blocks comprise on average from 2 to 100, e. g. from 4 to 50 alkylene oxide units, preferably ethylene oxide units, per molecule.

Suitable alkylene glycol fatty acid esters are alkylene glycol fatty acid mono esters, alkylene glycol fatty acid diesters, or mixtures of alkylene glycol fatty acid mono and diesters. A preferred alkylene glycol fatty acid mono ester is a propylene glycol fatty acid mono ester, such as propylene glycol laurates (available under the trade name LAUROGLYCOL®, namely LAUROGLYCOL® 90, or LAUROGLYCOL® FCC from Gattefossé, France). A preferred alkylene glycol fatty acid diester is a propylene glycol dicaprylocaprate (available under the trade name LABRAFAC® PG from Gattefossé, France).

Suitable sorbitan fatty acid esters are sorbitan monolaurate, sorbitan monopalmitate, sorbitan monostearate, sorbitan monooleate, sorbitan tristearate, sorbitan trioleate, sorbitan monostearate, sorbitan monolaurate or sorbitan monooleate.

Examples of suitable polyalkoxylated sorbitan fatty acid esters are polyoxyethylene (20) sorbitan monolaurate, polyoxyethylene (20) sorbitan monopalmitate, polyoxyethylene (20) sorbitan monostearate, polyoxyethylene (20) sorbitan monooleate, polyoxyethylene (20) sorbitan tristearate, polyoxyethylene (20) sorbitan trioleate, polyoxyethylene (4) sorbitan monostearate, polyoxyethylene (4) sorbitan monolaurate or polyoxyethylene (4) sorbitan monooleate.

Suitable polyalkoxylated glycerides are obtained for example by alkoxylation of natural or hydrogenated glycerides or by transesterification of natural or hydrogenated glycerides with polyalkylene glycols. Commercially available examples are polyoxyethylene glycerol ricinoleate 35, polyoxyethylene glycerol trihydroxystearate 40 (Cremophor® RH40, BASF AG) and polyalkoxylated glycerides like those obtainable under the proprietary names Gelucire® and Labrafil® from Gattefosse, e.g. Gelucire® 44/14 (lauroyl macrogol 32 glycerides prepared by transesterification of hydrogenated palm kernel oil with PEG 1500), Gelucire® 50/13 (stearoyl macrogol 32 glycerides, prepared by transesterification of hydrogenated palm oil with PEG 1500) or Labrafil M1944 CS (oleoyl macrogol 6 glycerides prepared by transesterification of apricot kernel oil with PEG 300).

A suitable fatty acid ester of polyalkylene glycols is, for example, PEG 660 hydroxystearic acid (polyglycol ester of 12-hydroxystearic acid (70 mol %) with 30 mol % ethylene glycol).

Suitable polyalkoxylated ethers of fatty alcohols are, for example, macrogol 6 cetylstearyl ether or macrogol 25 cetylstearyl ether Preferred among the non-ionic surfactants is a propyleneglycol fatty acid mono or diester or a mixture thereof.

In preferred embodiments, the non-ionic surfactant has an HLB of 4 or less, preferably 3.5 or less, most preferred 2.5 or less. The HLB system (Fiedler, H. B., Encylopedia of Excipients, $5^{th}$ ed., Aulendorf: ECV-Editio-Cantor-Verlag (2002)) attributes numeric values to surfactants, with lipophilic substances receiving lower HLB values and hydrophilic substances receiving higher HLB values. A preferred surfactant having an HLB value of about 2 is a propylene glycol dicaprylocaprate (available under the trade name LABRAFAC® PG). As shown in the examples that follow, the incorporation of the non-ionic surfactant having an HLB of 4 or less allows for the manufacture of an imatinib dosage form with essentially pH-independent drug release.

A plasticizer may be incorporated into the melt-processed mixture in order to decrease the glass transition temperature and the melt viscosity of the polymeric binder.

Plasticizers useful in the present invention comprise organic, preferably involatile compounds, such as, for example, $C_7$-$C_{30}$-alkanols, ethylene glycol, propylene glycol, glycerol, trimethylolpropane, triethylene glycol, butandiols, pentanols such as pentaerythritol and hexanols, polyalkylene glycols, preferably having a molecular weight of from 200 to 1 000, such as, for example, polyethylene glycols (e.g. PEG 300, PEG 400), polypropylene glycols and polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters, in particular triethylcitrate), fatty acid esters such as glycerol mono-, di- or triacetate or sodium diethyl sulfosuccinate. Particularly preferred plasticizers are selected from the group consisting of glyceryl triacetate, triethyl citrate, polyethylene glycol and mixtures thereof.

It is preferred that the amount of plasticizer is less than 20% by weight, preferably less than 10% by weight based on the total weight of the melt-processed mixture.

The melt-processed mixture may comprise optional ingredients. These optional ingredients include pharmaceutically acceptable fillers, disintegrants, lubricants, glidants, colorants, flavours and preservatives. These terms of the art are generally known to the skilled person. These optional ingredients are selected such that they are compatible with the active ingredient(s) and the other ingredients used.

Preferably, one or more glidants are used in the melt-processed mixture. As glidants, one or more of the following may be used: colloidal silica, e. g. Aerosil® 200, magnesium trisilicat, powdered cellulose, starch, talc, magnesium and calcium stearates, sodium stearyl fumarate, and the like. Preferably colloidal silica or/and sodium stearyl fumarate are used. The glidant is suitably used in an amount of 0.05 to 5% by weight based on the total weight of the melt-processed mixture.

"Melt-processing" means a transition into a viscous or pasty state in which it is possible for one component to become homogeneously embedded in the other. The melt-processing yields a cohesive mouldable mass. Usually melt-processing involves heating a mixture of the above specified components to a temperature above the softening temperature of the polymeric binder. The softening temperature may be somewhat lower than the intrinsic softening temperature of the polymeric binder due to the presence of plasticizers and/or fact that the non-ionic surfactant may exert a plasticizing effect. The softening temperature can be defined as the temperature at which the polymeric binder experiences a change in the rate of viscosity decrease as a function of temperature. During the melt-processing step the heating temperature does not exceed the melting temperature of the imatinib or imatinib salt.

Mixing of the components can take place before, during or after heating. For example, the components can be mixed first and then melted or simultaneously mixed and melted. Usually, the mass is homogenized in order to disperse the active ingredients efficiently. Also, it may be convenient first to melt the polymeric binder and then to admix and homogenize the active ingredients.

Usually, the temperature at which the melt-processing is carried out is in the range of 70 to 250° C., preferably 80 to 180° C., most preferably 100 to 140° C.

Melt-processing takes place in an apparatus customary for this purpose. Particularly suitable are extruders or kneaders. Suitable extruders include single screw extruders, intermeshing screw extruders or else multiscrew extruders, preferably twin screw extruders, which can be corotating or counterrotating and, optionally, equipped with kneading disks or other screw elements for mixing or dispersing the melt. It will be appreciated that the working temperatures will also be determined by the kind of extruder or the kind of configuration within the extruder used. Part of the energy needed to melt and mix the components in the extruder can be provided by heating elements. However, the friction and shearing of the material in the extruder may also provide a substantial amount of energy to the mixture and aid in the formation of a homogeneous melt of the components. Vacuum may be applied in at least one section of the extruder in order to remove residual solvents, e. g. water, in order to prevent incompatibilities between excipients and active ingredient or negative impacts on the stability of the formulation, e. g. hardness of single dose units, or degradation of the active ingredient.

Melt-processing is preferably carried out by melt-extrusion, i.e., by use of an extruder. The melt-extrusion process comprises the steps:

(a) mixing and heating imatinib or a salt thereof, at least one polymeric binder, and at least one pharmaceutically acceptable non-ionic surfactant, and optionally further ingredients to obtain a cohesive mouldable mass; and (b) forcing the mass through a die.

According to the invention, the cohesive mouldable mass is preferably direct-shaped. The term "direct-shaping" is intended to mean a process which involves bringing the mass directly into the desired shape of the dosage form; and allowing the mass to solidify. Such process is in contrast to the conventional way of using a granulate (e. g., a granulate obtained by a wet-granulation process or a granulate obtained by a melt-granulation process), which is then admixed with excipients and compressed or compacted to form a tablet.

Evidently, the advantage of the direct-shaping process lies in the elimination of several process steps. Compression/compaction-moulded tablets typically are characterized by having an inner phase (corresponding to the preformed granulate particles) and an outer phase surrounding and holding together the inner phase. Apart from inhomogeneities already present in the cohesive moldable mass, direct-shaped dosage forms essentially consist of a single phase.

Several direct-shaping processes are known to the skilled person among which calendering, injection-moulding, and thermoforming processes are preferred.

Calendering denotes a process wherein the cohesive mouldable mass is introduced into a calender with two counter-rotating rollers with mutually matching depressions on their surface. A broad range of dosage forms can be attained by using rollers with different forms of depressions. Suitable processes are described in e. g. EP 0799013, EP 0802779, or EP 1135092.

Injection-moulding denotes a process wherein the mouldable mass is injected at high pressure into a mould, which is the inverse of the desired shape. Suitable methods are described in WO 01/43943.

Thermoforming denotes a process wherein a powdery mixture is placed in a mould cavity and heated to a forming temperature to induce sintering of the mixture. The thus formed cohesive mouldable mass adopts the shape of the mould cavity. The moulded dosage form is subsequently solidified. The deformation of the mixture may be assisted by the use of a heated punching tool. Suitable methods are described in WO 05/016313.

The dosage forms may vary in shape and be, for example, round, oval, oblong, cylindrical or any other suitable shape. In order to facilitate the intake of such a dosage form by a mammal, it is advantageous to give the dosage form an appropriate shape. Large tablets that can be swallowed comfortably are therefore preferably elongated rather than round in shape.

A film coat on the dosage form further contributes to the ease with which it can be swallowed. A film coat also improves taste and provides an elegant appearance. If desired, the film coat may be an enteric coat. The film coat usually includes a polymeric film-forming material such as hydroxypropyl methylcellulose, hydroxypropylcellulose, and acrylate or methacrylate copolymers. Besides a film-forming polymer, the film-coat may further comprise a plasticizer, e.g. polyethylene glycol, a surfactant, e.g. a Tween® type, and optionally a pigment, e.g. titanium dioxide or iron oxides. The film-coating may also comprise talc as an anti-adhesive. The film coat usually accounts for less than about 5% by weight of the dosage form.

The dosage forms according to the invention exhibit improved abrasion resistance and hardness.

The dosage forms according to the invention are useful for human indication of imatinib, such as anti-tumor treatment, e. g. treatment of non-malignant and malignant proliferative disorders, e. g. leukemias, gliomas, sarcomas, prostate-, breast-, gastro- intestinal-, lung-, ovary tumors.

The accompanying figures and the following non-limitative examples illustrate the invention.

FIGS. 1 to 5 show the drug release of dosage forms according to the invention at different pH values.

EXAMPLES

The components indicated in the table I below were blended using a high shear mixer. Liquid excipients were granulated with the solid raw materials. The powdery mixture was then fed into a twin-screw extruder (Rheomex PTW 16, Thermo Electron, Karlsruhe, Germany) at a rate of 0.8 kg/h and a processing temperature of 130° C. The extrudate was fed to a calender with two counter-rotating rollers having mutually matching cavities on their surfaces. Oblong tablets of approximately 1200 mg (corresponding to 800 mg imatinib free base) of 18.8 mm length and 9.55 mm diameter were thus obtained.

The release properties of the resulting dosage forms were measured with a dissolution apparatus (rotating basket) according to USP at 100 rpm and 37° C. The volume of the dissolution medium was 900 mL. As dissolution media hydrochloric acid 0.1 mol/L (pH 1.0); sodium acetate 50 mmol/L (pH 4.5) and potassium dihydrogen phosphate 50 mmol/L (pH 6.8) were used. Samples of 10 mL were withdrawn at 0.5, 1, 2, 3, 4, 6 and 8 hours. After dilution with an appropriate volume of 0.1 mol/L hydrochloric acid the samples were analysed by UV spectrophotometry at 264 nm.

The results of the dissolution studies are shown in FIGS. 1 to 5.

TABLE I

| Ingredient | Example 1 | Example 2 | Example 3 | Example 4 | Example 5 |
|---|---|---|---|---|---|
| Imatinib mesylate | 80 | 80 | 80 | 80 | 80 |
| Klucel EF[1] | 10 | 10 | | | 10 |
| Klucel MF[1] | | | 10 | | |
| Ethocel V100[2] | 2 | 1 | | | |
| Kollidon SR[3] | | | | 12 | |
| Lauroglycol FCC[4] | 7 | | 7 | | |
| Lauroglycol 90[4] | | | | | 7 |
| Labrafac PG[5] | | 7 | | 5 | |
| Sodium stearylfumarate | 1 | 2 | 3 | 3 | 3 |

[1]Hydroxypropyl cellulose
[2]Ethylcellulose
[3]Polyvinylacetate 80/Polyvinylpyrrolidone 19
[4]Propyleneglycol monolaurate
[5]Propyleneglycol dicaprylocaprate

We claim:

1. A dosage form, comprising a melt-processed mixture of
 (a) a pharmaceutically effective amount of imatinib or a salt thereof,
 (b) at least one polymeric binder, and
 (c) at least one pharmaceutically acceptable non-ionic surfactant having an HLB of 3.5 or less, wherein the non-ionic surfactant is a polyol fatty acid ester, a polyalkoxylated polyol fatty acid ester, a polyalkoxylated fatty alcohol ether or a mixture thereof.

2. The dosage form of claim 1, wherein imatinib or a salt thereof is present in an amount of at least 50% by weight based on the total weight of the melt-processed mixture.

3. The dosage form of claim 1, which is direct-shaped.

4. The dosage form of claim 3, wherein direct-shaping is carried out by calendering, injection-moulding, or thermoforming.

5. The dosage form of claim 1, wherein the drug release from the dosage form is essentially independent of pH.

6. The dosage form of claim 1, wherein the drug release at 8 hours results in a ratio of a release value at pH 6.8 relative to a release value at pH 1.0 of at least 0.6.

7. The dosage form of claim 1, wherein the non-ionic surfactant is a propyleneglycol fatty acid mono- or diester or a mixture thereof.

8. The dosage form of claim 1, wherein the non-ionic surfactant has an HLB of 2.5 or less.

9. The dosage form of claim 1, wherein the polymeric binder is selected from the group consisting of cellulose esters, cellulose ethers and homo- or copolymers of vinylpyrrolidone, and mixtures thereof.

10. A method for preparing the dosage form of claim 1, the method comprising
   (a) mixing and heating imatinib or a salt thereof, at least one polymeric binder, and at least one pharmaceutically acceptable non-ionic surfactant having an HLB of 3.5 or less, and optionally further ingredients to obtain a cohesive mouldable mass, wherein the non-ionic surfactant is a polyol fatty acid ester, a polyalkoxylated polyol fatty acid ester, a polyalkoxylated fatty alcohol ether or a mixture thereof; and
   (b) forcing the mass through a die.

11. The method of claim 10, comprising bringing the cohesive mouldable mass directly into the desired shape of the dosage form.

12. The dosage form of claim 9, wherein the cellulose ether is methylcellulose, ethyl cellulose, hydroxyalkylcellulose or hydroxyalkylalkylcellulose.

13. The dosage form of claim 12, wherein the hydroxyalkylcellulose is hydroxyproplylcellulose.

14. The dosage form of claim 12, wherein the hydroxyalkylalkylcellulose is hydroxyproplymethylcellulose.

15. The dosage form of claim 9, wherein the cellulose ester is selected from the group consisting of cellulose phthalates and cellulose succinates.

16. The dosage form of claim 15, wherein the cellulose phthalate is cellulose acetate phthalate, hydroxyproplylmethlycellulose phthalate or hydroxyproplylmethylcellulose acetate phthalate.

17. The dosage form of claim 15, wherein the cellulose succinate is hydroxyproplylmethlycellulose succinate or hydroxyproplylmethylcellulose acetate succinate.

* * * * *